United States Patent
Mire

(10) Patent No.: US 7,051,378 B1
(45) Date of Patent: May 30, 2006

(54) THREE DIGIT MEDICAL GLOVE

(76) Inventor: Blane A. Mire, 209 Glenwood Dr., Natchez, MS (US) 39120

( * ) Notice: Subject to any disclaimer, the term of this patent is extended or adjusted under 35 U.S.C. 154(b) by 63 days.

(21) Appl. No.: 11/065,010

(22) Filed: Feb. 24, 2005

(51) Int. Cl.
*A41D 19/00* (2006.01)

(52) U.S. Cl. .......................................... 2/161.7; 2/163

(58) Field of Classification Search ................. 2/161.7, 2/163, 161.6
See application file for complete search history.

(56) References Cited

U.S. PATENT DOCUMENTS

| | | | |
|---|---|---|---|
| 2,083,604 A | 6/1937 | Hay | |
| 2,847,676 A | 8/1958 | Scott | |
| 4,534,066 A | 8/1985 | Hansson | |
| 4,916,757 A | 4/1990 | Berlin et al. | |
| 5,636,382 A * | 6/1997 | Chopko et al. | 2/167 |
| 2002/0010957 A1 | 1/2002 | Katz | |

* cited by examiner

*Primary Examiner*—Katherine M. Moran

(57) ABSTRACT

A three digit medical glove for easy placement over a conventional five digit glove, the three digit medical glove of the invention including a thumb section, an index finger section, a middle finger section, and a generally rectangular palm portion, the palm portion having an upper end, a lower end, and two sides connecting the upper end to the lower end, the palm portion being connected at the upper end to the index finger section and the middle finger section, the palm portion having an enclosed upper surface extending generally horizontally from the base of the middle finger section to the other of the two sides of the palm portion, the palm portion beneath the enclosed upper surface of the palm portion being adapted to receive and enclose the folded little finger and ring finger of the hand.

4 Claims, 2 Drawing Sheets

THREE DIGIT MEDICAL GLOVE

BACKGROUND OF THE INVENTION

1. Field of the Invention

The present invention relates to medical examination gloves. In particular, the present invention is related to disposable medical examination gloves used in medical examinations wherein a first glove is placed on one hand of a medical examiner and a second glove is placed over the first glove.

2. Description of the Related Art

Medical examination gloves are well known in the art. Such gloves are elastic and stretch outward when the hand of the medical examiner is inserted therein to insure a snug fit over the fingers, thumb, palm, and wrist of the medical examiner. Various polymeric materials well known in the art are used to form medical examination gloves.

Medical examination procedures are common in which a first glove is placed on a hand of the medical examiner and a second glove is placed over the first glove. Such procedures are commonly referred to as "double gloving".

The two most common medical examinations utilizing double gloving are digital medical examinations associated with gastrointestinal endoscopy and gynecological examinations. In gastrointestinal endoscopy examinations, an initial digital examination is performed to the rectum prior to placement of the endoscope in the rectum. The top glove is then removed to expose the clean first or bottom glove used to perform the endoscopy procedure. In gynecological examinations, an initial digital examination is made of the vaginal vault. The top glove is then removed to expose the clean first or bottom glove and a digital rectal examination is made with the clean glove.

Difficulty is encountered in placing a typical five digit glove over the top of the first glove placed on the hand of the medical examiner. The coefficient of friction between the five digit top glove and the bottom five digit glove prevents the top glove from sliding easily over the bottom glove. The top glove sticks to the bottom glove, requiring the top glove to be carefully aligned with the bottom glove, and each digit of the top glove must be carefully forced over the corresponding digit of the bottom glove. Often, to expedite placement of the top glove over the bottom glove, the medical examiner will only insert the digits necessary for performing the first medical exam into the top glove, such as the thumb, index finger, and the middle finger. The other two fingers in the bottom glove, the little finger and the ring finger, are not inserted into the top glove, and the ring finger and little finger sections of the top glove are left flopping or pulled into the palm with the thumb. The most important digits to be used in the rectal or vaginal exam prior to discarding the top glove are the thumb, index finger, and middle finger.

Exemplary of the related art are the following U.S. Pat. Nos. 4,916,757; 4,534,066; 2,847,676; and 2,083,604; and U.S. Patent Application Publication US.

BRIEF SUMMARY OF THE INVENTION

In accordance with the present invention there is provided a three digit medical glove for easy placement over a conventional five digit glove, the three digit medical glove of the invention including a thumb section for receipt and enclosure of the thumb of the medical examiner, the thumb section having a base and a distal end, an index finger section for receipt and enclosure of the index finger of the medical examiner, the index finger section having a base and a distal end, a middle finger section for receipt and enclosure of the middle finger of the medical examiner, the middle finger section having a base and a distal end, and a generally rectangular palm portion for receipt and enclosure of the palm of the hand, the generally rectangular palm portion having an upper end, a lower end, and two sides connecting the upper end to the lower end, the palm portion being connected at the upper end to the index finger section and the middle finger section, the thumb section being connected to one of the two sides, the palm portion having an enclosed upper surface extending generally horizontally from the base of the middle finger section to the other of the two sides of the palm portion, the palm portion beneath the enclosed upper surface of the palm portion being adapted to receive and enclose the folded little finger and ring finger of the hand of the medical examiner, the palm portion having an opening in the lower end thereof for insertion of the hand of the medical examiner.

DETAILED DESCRIPTION OF THE INVENTION

Figure 1:
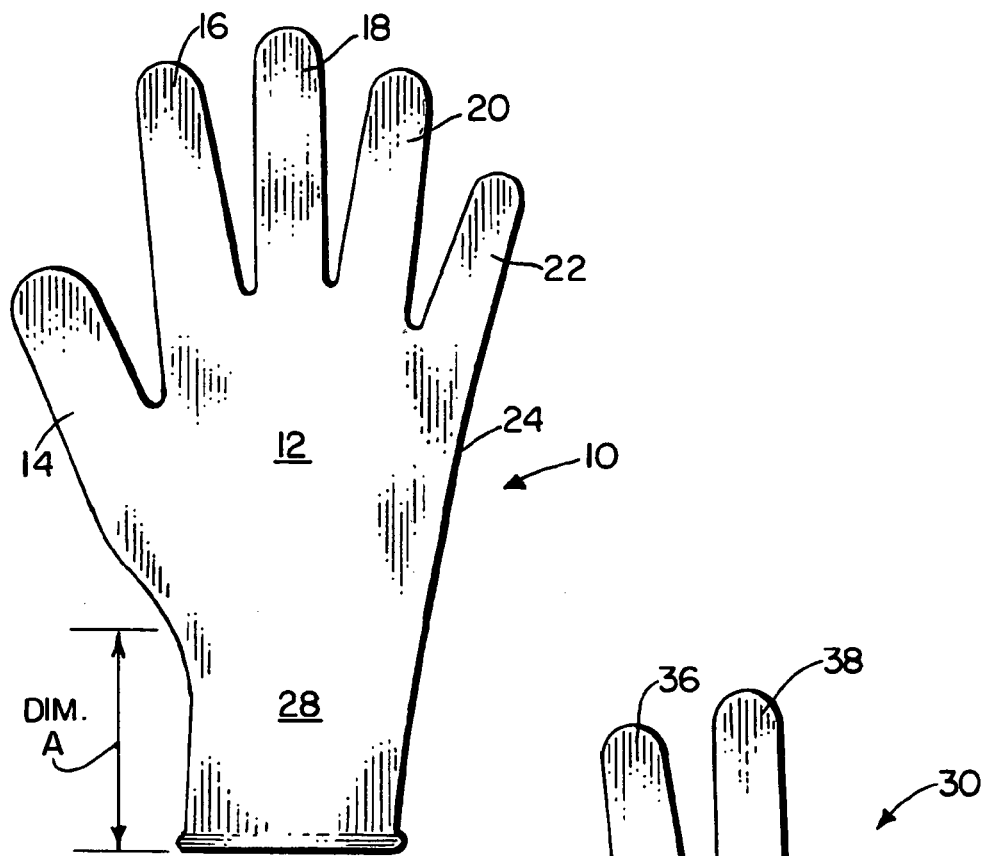
FIG. 1 is a plan view of the medical glove of the prior art.

Referring now to the drawings, and in particular to FIG. 1, an elastic medical examination glove of the prior art is generally indicated by the numeral 10. Glove 10 has a generally rectangular palm portion indicated by the numeral 12 for receiving and enclosing the palm of the hand of a user such as a medical examiner. Connected to the top of palm portion 12 is an index finger section 16 for receipt and enclosure of the index finger, a middle finger section 18 for receipt and enclosure of the middle finger, a ring finger section 20 for receipt and enclosure of the ring finger, and a little finger section 22 for receipt and enclosure of the little finger. Each of the finger sections 16, 18, 20, and 22 are connected at their base to the top of palm portion 12 and extend outward to their distal ends. Thumb section 14 is connected at its base to the side of palm portion 12 and extends outward to its distal end.

Palm portion 12 has a generally vertical side surface 24 extending downward to ring 26. Ring 26 surrounds the opening in the bottom of glove 10 for insertion of the hand of the medical examiner. Ring 26 is commonly molded integrally with the elastic, polymeric material from which medical examination glove 10 of the prior art is formed and may be grasped by the fingers of one hand to pull the glove on and remove the glove from the other hand.

Glove 10 has a wrist portion generally indicated by the numeral 28 which extends downward from palm portion 12 and covers the wrist and upper forearm of the medical examiner. Wrist portion extends downward from the base of thumb section 14 a distance indicated in FIG. 1 as DIM. A. DIM. A is commonly about two inches in length.

Glove 10 stretches over and completely encloses the hand of a medical examiner. Glove 10 is available in various sizes to form a snug fit over the hand of individual medical examiners.

Double gloving medical examination procedures in which a first glove such as glove 10 is placed on a hand of the medical examiner and a second glove such as glove 10 is placed over the first glove. Double gloving procedures cause difficulty for the medical examiner in placing the second five digit glove over the first five digit glove. The three digit gloves of the invention shown in FIGS. 2, 3, 4, 5A, and 5B reduce the difficulty and frustration encountered by medical examiners performing a double gloving procedure in placing a second glove over a first glove.

Figure 2:
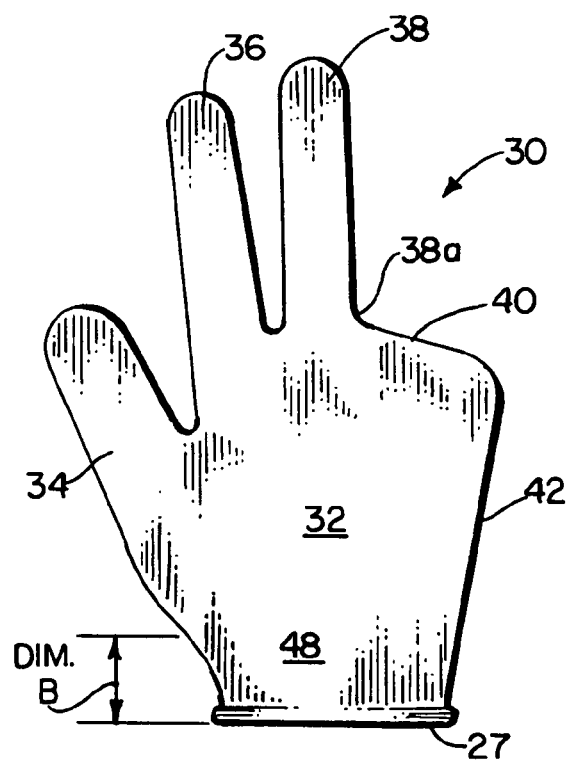
FIG. 2 is a plan view of a preferred embodiment of the three digit medical glove of the invention.
Figures 3, 4:
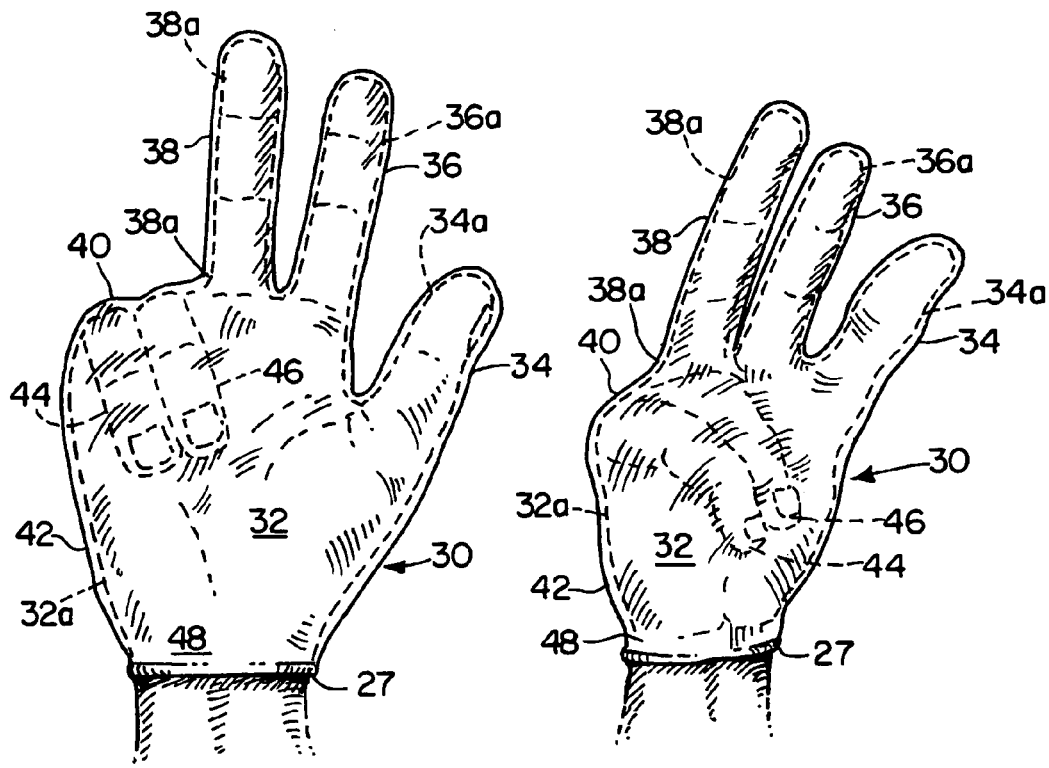
FIG. 3 is a plan view of the medical glove of the invention on the hand of the user with the hand shown in phantom lines.
FIG. 4 is a perspective view of the medical glove of the invention on the hand of the user with the hand shown in phantom lines.

Referring now to FIGS. 2–4, the three digit elastic medical examination glove of the invention is generally indicated by the numeral 30. Three digit glove 30 stretches over and encloses the hand of a medical examiner wearing a five digit medical examination glove such as glove 10 of the prior art shown in FIG. 1. For purposes of clarity of illustration, glove 10 is not shown to be worn on the hand inside glove 30 in FIGS. 3 and 4.

Glove 30 has a generally rectangular palm portion indicated by the numeral 32 for receiving and enclosing the palm 32a of the hand of a medical examiner shown in phantom lines in FIGS. 3 and 4. Connected to the top of rectangular palm portion 32 and extending generally vertically upward therefrom are index finger section 36 for receipt and enclosure of the index finger 36a and middle finger section 38 for receipt and enclosure of the middle finger 38a. Each of the finger sections 36 and 38 are connected at their base to the top of palm portion 32 and extend outward to their respective distal ends. Connected at its base to the side of palm portion 32 is thumb section 34 for receipt and enclosure of the thumb 34a. Thumb section 34 extends outward from the side of palm portion 32 to the distal end of thumb section 34.

Palm portion 32 has an enclosed upper surface 40 at the top thereof which extends generally horizontally from the base 38a of middle finger section 38 to the side surface 42 of palm portion 32. Upper surface 40 is of sufficient length to cover the folded little finger 44 and ring finger 46 of the user as shown in FIGS. 3 and 4.

Palm portion 32 has a generally vertical side surface 42 extending downward perpendicularly to ring 27. Ring 27 surrounds the opening in the bottom of glove 32 for insertion of the hand of the medical examiner into glove 30. Ring 27 is preferably molded integrally with the elastic, polymeric material from which medical examination glove 30 is formed and may be grasped by the fingers of one hand to pull glove 30 on and remove the glove 30 from the other hand.

Glove 30 has a wrist portion generally indicated by the numeral 48 which extends downward from palm portion 32 to the wrist of the medical examiner. Wrist portion extends downward from the base of thumb section 14 a distance indicated in FIG. 1 as DIM. A to ring 27. DIM. A is commonly about two inches in length in gloves of the prior art such as glove 10. Preferably, to enable the easy removal of glove 30 from the hand of a medical examiner wearing a conventional medical glove such as glove 10, DIM. A is minimized and preferably may be one centimeter or less.

Figures 5A, 5B:
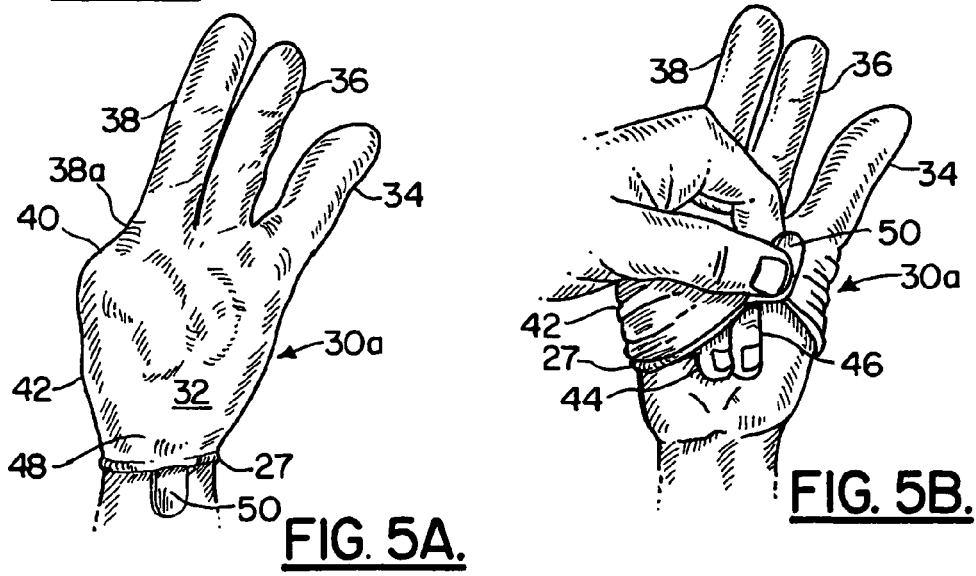
FIG. 5A is a perspective view of an alternate embodiment of the medical glove of the invention on the hand of the user.
FIG. 5B is a perspective view of an alternate embodiment of the medical glove of the invention on the hand of the user showing removal of the glove from the hand of the user.

Referring now to FIGS. 5A and 5B, an alternate embodiment of the three digit glove of the invention is shown and generally indicated by the numeral 30a. Glove 30a stretches over and covers the hand of a medical examiner wearing a medical examination glove such as glove 10 of the prior art shown in FIG. 1. For purposes of clarity of illustration, glove 10 is not shown to be worn on the hand under glove 30a in FIGS. 3 and 4.

As can be seen in the drawings, glove 30a is identical to glove 30 with the exception of the addition of a tab 50 to ring 27. Tab 50 is of sufficient size and shape to be grasped by the fingers of the hand on which glove 30a is not worn and pulled upward as shown in FIG. 5B to remove glove 30a from the hand on which glove 30a is worn, or tab 50 could be grasped by the fingers of the hand on which glove 30a is not worn and pulled downward to pull glove 30a onto the hand on which a typical glove 10 is worn. A portion of rib 27 could be omitted if desired and tab 50 could be attached to the bottom of the wrist portion 48 of glove 30a where the rib is omitted.

Gloves 30 and 30a are elastic and stretch outward when the hand of the user is inserted therein to insure a snug fit over the fingers, thumb, palm, and wrist. Various polymeric materials well known in the art to make the glove 10 of the prior art may be used to form the medical examination gloves 30 and 30a of the invention. If desired, thumb section 34 could be sized larger than the thumb of the wearer for quicker and easier application of the gloves 30 and 30a.

Although the preferred embodiments of the invention have been described in detail above, it should be understood that the invention is in no sense limited thereby, and its scope is to be determined by that of the following claims:

What is claimed is:

1. An elastic three digit medical examination glove for placement over a first elastic five digit medical examination glove worn on the hand of a medical examiner, said glove comprising:
   a. a thumb section for receipt and enclosure of the thumb of said medical examiner, said thumb section having a base and a distal end,
   b. an index finger section for receipt and enclosure of the index finger of said medical examiner, said index finger section having a base and a distal end, c. a middle finger section for receipt and enclosure of the middle finger of said medical examiner, said middle finger section having a base and a distal end, and d. a generally rectangular palm portion for receipt and enclosure of the palm of said hand, said generally rectangular palm portion having an upper end, a lower end, and two sides connecting said upper end to said lower end, said palm portion being connected at said upper end to said base of said index finger section and to said base of said middle finger section, said thumb section being connected to one of said two sides, said palm portion having an enclosed upper surface extending generally horizontally from said base of said middle finger section to the other of said two sides of said palm portion, said palm portion beneath said enclosed upper surface of said palm portion being adapted to receive and enclose the folded little finger and ring finger of said hand of said medical examiner, said palm portion having an opening in said lower end thereof for insertion of said hand of said medical examiner.

2. The glove of claim 1 wherein said lower end of said palm portion has a ring connected thereto for grasping with the fingers of a hand.

3. The glove of claim 2 wherein said ring has a tab connected thereto for grasping with the fingers of a hand.

4. The glove of claim 1 wherein said lower end of said palm portion has a tab connected thereto for grasping with the fingers of a hand.

* * * * *